United States Patent
Kim

(10) Patent No.: US 10,856,817 B2
(45) Date of Patent: Dec. 8, 2020

(54) DEVICE OF DETECTION FOR MORPHOLOGICAL FEATURE EXTRACTION FROM ARTERIAL BLOOD PRESSURE WAVEFORM AND DETECTION METHOD FOR THE SAME

(71) Applicant: Korea University Research and Business Foundation, Seoul (KR)

(72) Inventor: Dong-Joo Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 364 days.

(21) Appl. No.: 15/564,778

(22) PCT Filed: Apr. 7, 2016

(86) PCT No.: PCT/KR2016/003673
§ 371 (c)(1),
(2) Date: Oct. 6, 2017

(87) PCT Pub. No.: WO2016/163787
PCT Pub. Date: Oct. 13, 2016

(65) Prior Publication Data
US 2018/0110473 A1 Apr. 26, 2018

(30) Foreign Application Priority Data

Apr. 8, 2015 (KR) .................. 10-2015-0049758

(51) Int. Cl.
*A61B 5/021* (2006.01)
*A61B 5/00* (2006.01)

(52) U.S. Cl.
CPC ............ *A61B 5/7278* (2013.01); *A61B 5/021* (2013.01); *A61B 5/7225* (2013.01);
(Continued)

(58) Field of Classification Search
None
See application file for complete search history.

(56) References Cited

U.S. PATENT DOCUMENTS

2013/0324859 A1* 12/2013 Park .................. A61B 5/02007
600/479

FOREIGN PATENT DOCUMENTS

JP       2001229767 A     8/2001
KR   10-2002-0002450 A    1/2002
(Continued)

*Primary Examiner* — Marjan Fardanesh
(74) *Attorney, Agent, or Firm* — Fox Rothschild LLP

(57) ABSTRACT

The present invention relates to a device and a method for detecting a feature of an arterial blood pressure (ABP) waveform. The feature detecting method of an ABP waveform according to an exemplary embodiment of the present invention includes: searching a peak and a trough; detecting a systolic peak based on a time interval between a peak and a neighboring peak and an average pressure value; detecting a pulse onset with respect to a trough directly before the systolic peak; extracting a candidate of a dicrotic notch based on a magnitude of the systolic peak and a measurement time; detecting a point having a lowest pressure value among candidates of the dicrotic notch as a dicrotic notch and detecting a dicrotic peak based on the dicrotic notch; and classifying the detected dicrotic notches into a normal notch and a transient notch.

9 Claims, 4 Drawing Sheets

(52) U.S. Cl.
CPC ............ *A61B 5/7264* (2013.01); *A61B 5/742* (2013.01); *A61B 5/02116* (2013.01); *A61B 5/4064* (2013.01); *A61B 5/4842* (2013.01); *A61B 5/7275* (2013.01)

(56) References Cited

FOREIGN PATENT DOCUMENTS

| KR | 10-2012-0058243 A | 6/2012 |
|---|---|---|
| KR | 10-1305964 B1 | 9/2013 |
| KR | 10-2014-0107407 A | 9/2014 |

\* cited by examiner

[FIG. 1]
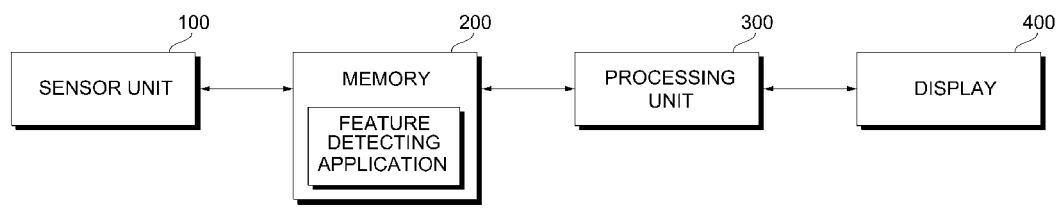
[FIG. 2]
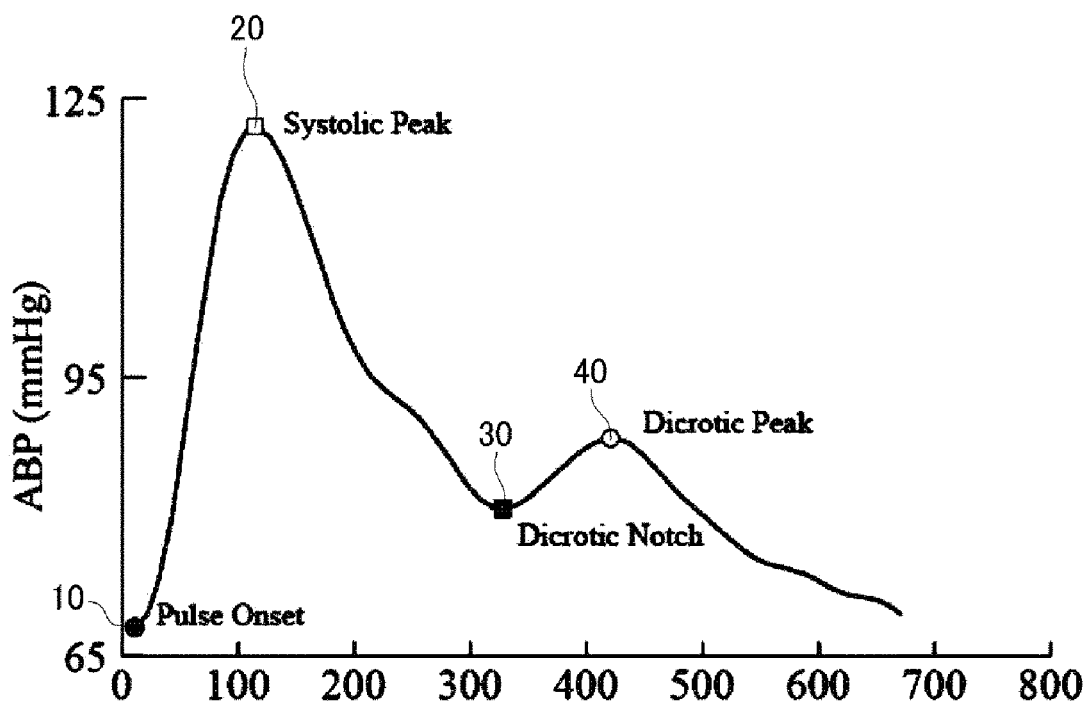

[FIG. 3]
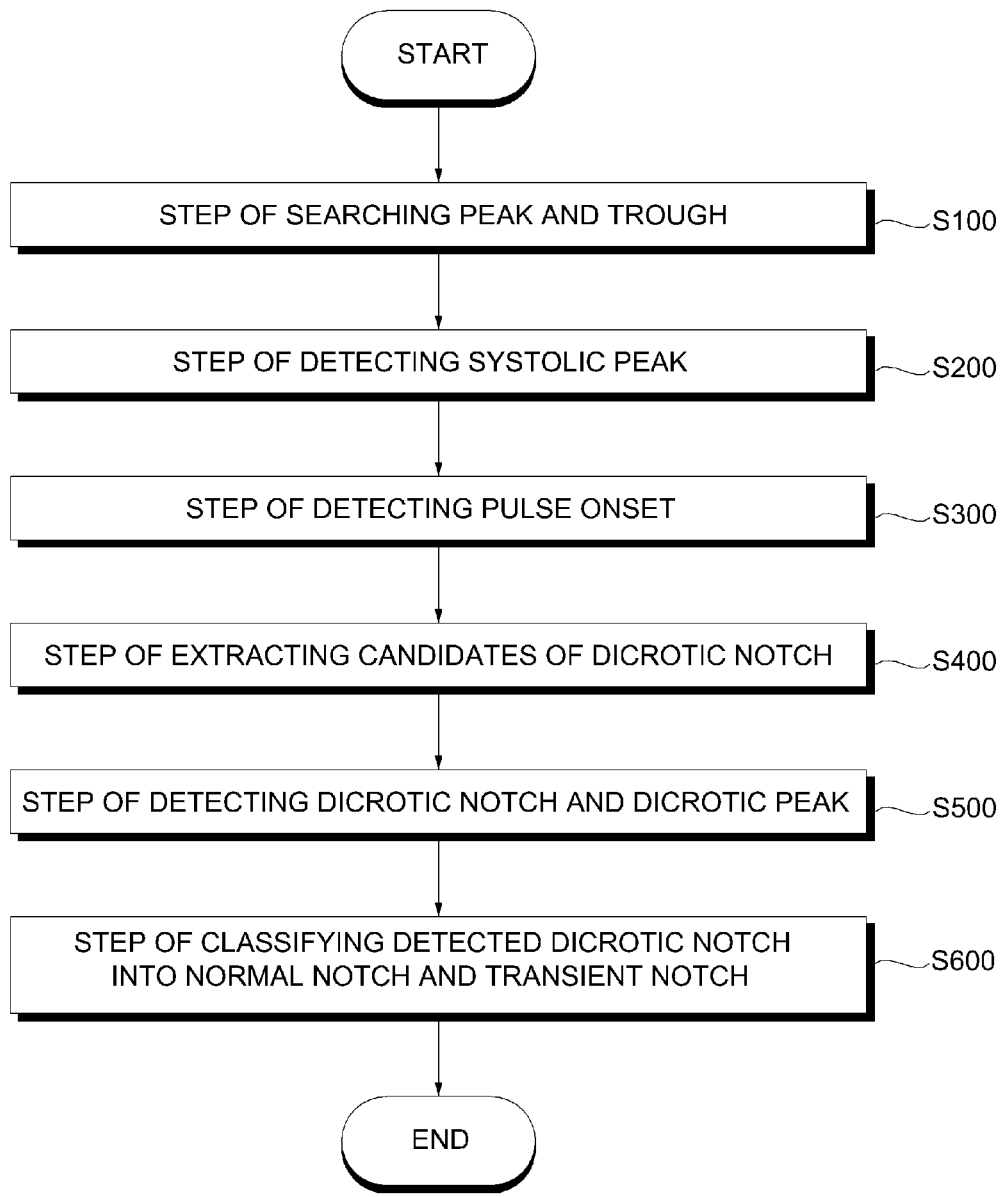

[FIG. 4]
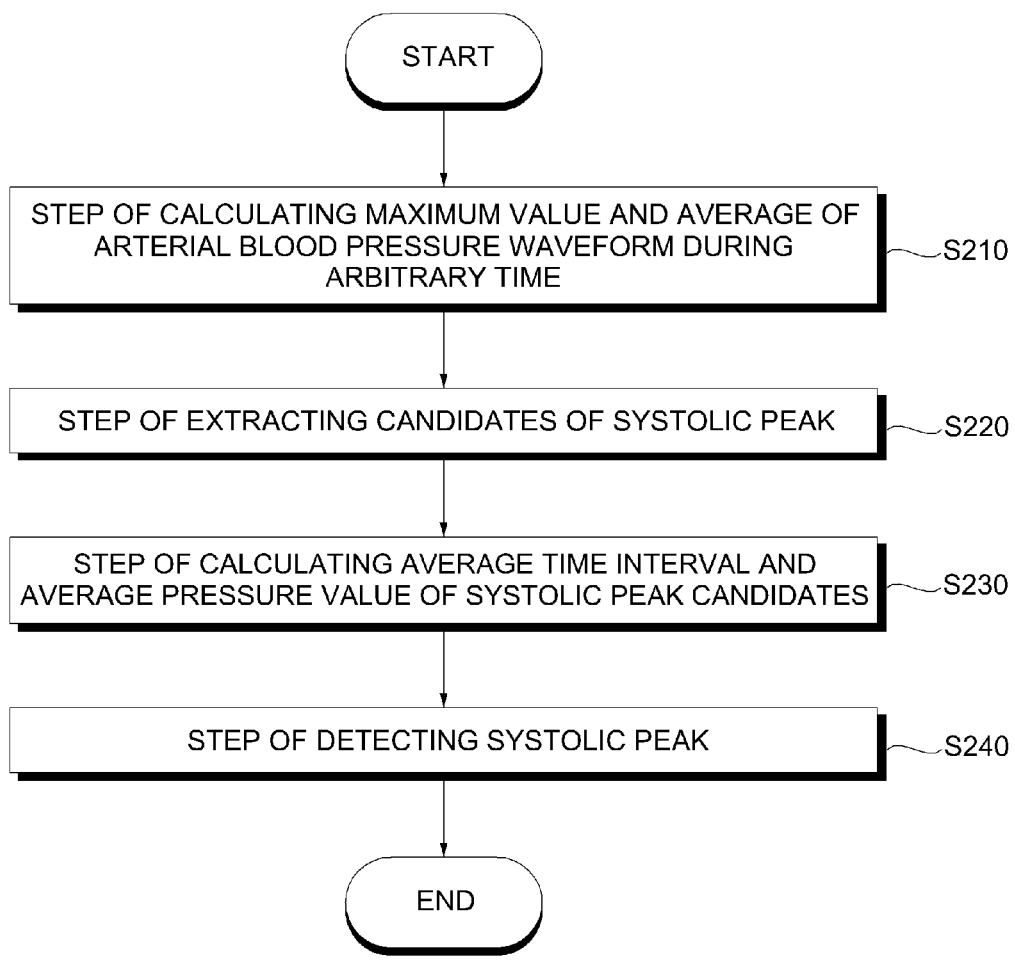

[FIG. 5]
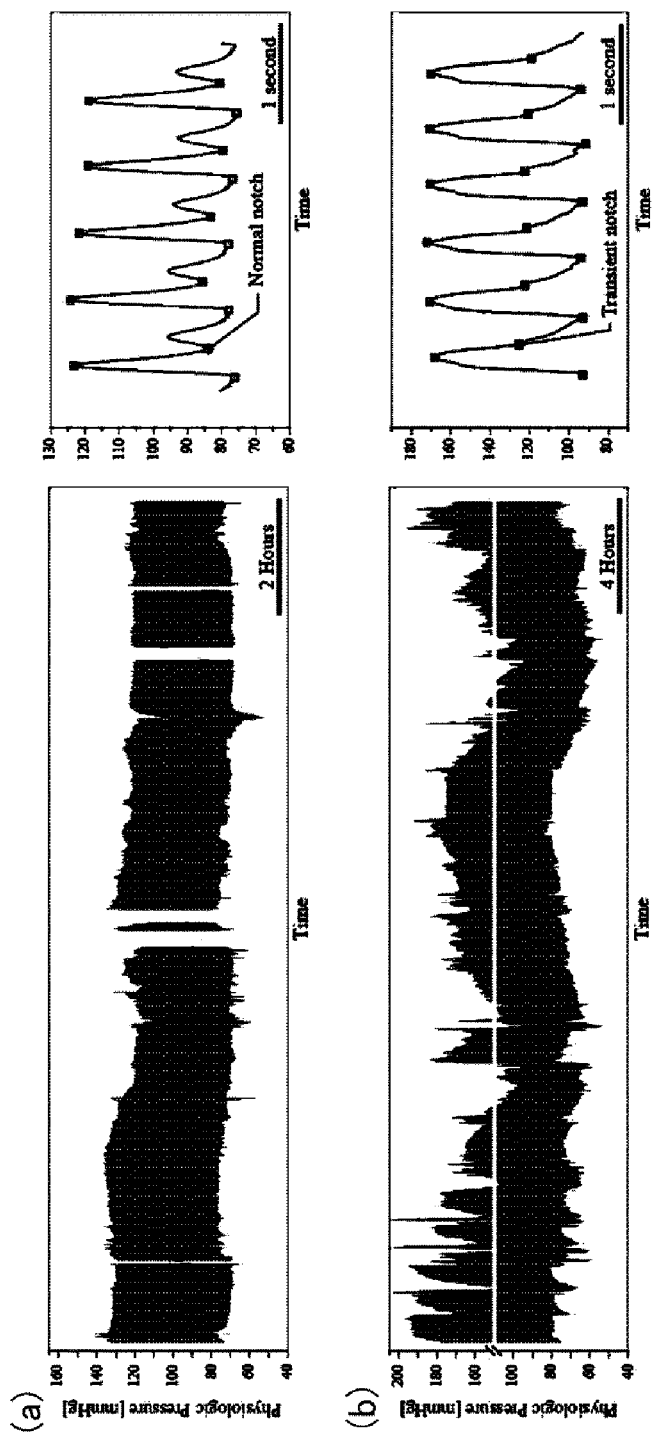

DEVICE OF DETECTION FOR MORPHOLOGICAL FEATURE EXTRACTION FROM ARTERIAL BLOOD PRESSURE WAVEFORM AND DETECTION METHOD FOR THE SAME

TECHNICAL FIELD

The present invention relates to a device and a method for detecting a feature of an arterial blood pressure waveform.

BACKGROUND ART

An arterial blood pressure (ABP) waveform is one of major parameters used in a clinical practice and provides cardiovascular information such as a heart rate, and stiffness of arterial blood vessels. Further, parameters of cardiovascular diseases such as a cardiac output, an arterial compliance, and peripheral resistance may be obtained through the ABP waveform.

Specifically, diseases such as congestive heart failure, aorta insufficiency, and aorta stenosis have a specific ABP waveform. Therefore, when the ABP waveform is thoroughly monitored, it allows to precisely diagnose a patient and appropriately treat the patient and helps to evaluate an outcome and a prognosis of the patient.

As described above, the ABP waveform is closely related to blood circulation and analysis of the ABP waveform has been actively used for diagnosis of a condition of the heart. However, the ABP waveform reflects not only cardiovascular information, but also various cerebrovascular information.

Therefore, a cerebral perfusion pressure (CPP) which is considered as an indicator of a risk of a secondary brain damage such as cerebral ischemia of a patient with a brain damage may be calculated using a value obtained by subtracting an intracranial pressure (ICP) from an average ABP waveform. Nevertheless, there have been no studies on a method for utilizing the ABP waveform for diagnosis of a neuropathological condition, other than the method which uses an average of the ABP waveform.

As one of techniques for measuring a condition of the cerebrovascular system, a transcranial Doppler (TCD) which enables a brain blood flow examination is widely used. The TCD ultrasound examination suggests an indicator which indirectly reflects the condition of the cerebrovascular system by measuring a velocity of a blood flow using the Doppler Effect. However, in order to perform the brain blood flow examination, a probe needs to be in contact with the blood vessel and thus a measurement value varies by an incident angle of an ultrasound wave in accordance with the contact with the probe. Therefore, it is difficult to stably and consistently monitor the ABP waveform by the TCD examination.

With regard to this, Japanese Unexamined Patent Application Publication No. 2014-18272 (a blood pressure measuring device and a parameter correcting method for prediction of a central blood pressure) discloses a blood pressure measuring device which includes an input unit which inputs a blood pressure change of a peripheral artery measured by a blood pressure measuring device, a blood vessel cross-section indicator measuring unit which measures a change in a diameter of a blood vessel of a central artery or a blood vessel cross-section, and a correcting unit which uses a measuring result of a blood pressure measuring device and the blood vessel cross-section indicator measuring unit for a predetermined period in which a relationship between the blood vessel cross-section indicator and a blood pressure of a peripheral artery corresponds to a relationship between the blood vessel cross-section indicator and the central blood pressure for one heartbeat period and corrects a parameter related to a blood pressure predicting process which predicts a central blood pressure from the blood vessel cross-section indicator.

DISCLOSURE OF THE INVENTION

Technical Problem

The present invention has been made in an effort to solve the problem of the related art to provide a method for automatically extracting a feature from an ABP waveform.

However, technical objects to be achieved by the present exemplary embodiments are not limited to the technical objects as described above and other technical objects may be present.

Technical Solution

According to an aspect of the present invention, there is provided a feature detecting method of an ABP waveform including: searching a peak and a trough; detecting a systolic peak based on a time interval between a peak and a neighboring peak and an average pressure value; detecting a pulse onset with respect to a trough directly before the systolic peak; extracting a candidate of a dicrotic notch based on a magnitude of the systolic peak and a measurement time; detecting a point having a lowest pressure value among candidates of the dicrotic notch as a dicrotic notch and detecting a dicrotic peak based on the dicrotic notch; and classifying the detected dicrotic notch into a normal notch and a transient notch.

According to another aspect of the present invention, there is provided a feature detecting device of an ABP waveform including: a memory in which a feature detecting application of an ABP waveform is stored; and a processing unit which is aligned to interface with the feature detecting application. In this case, the processing unit receives an ABP waveform from a sensor unit and converts the received ABP waveform signal into digital data to store the converted digital data in the memory, according to the execution of the feature detecting application, searches a peak and a trough from the ABP waveform, detects a systolic peak based on an time interval between a peak and a neighboring peak and an average pressure value and detects a pulse onset with respect to a trough directly before the systolic peak, and then extracts a candidate of a dicrotic notch based on a magnitude of the systolic peak and a measurement time to detect a point having a lowest pressure value among candidates of the dicrotic notch as a dicrotic notch, and detects a dicrotic peak based on the dicrotic notch, and then classifies the detected dicrotic notch into a normal notch and a transient notch.

Advantageous Effects

According to any one of the above-described solving means of the present invention, the feature of the ABP waveform is automatically detected so that the ABP waveform may be consistently and directly monitored.

Further, the present invention may be usefully used to rapidly and precisely predict a clinical situation, specifically, diagnosis and prognosis of a patient with a brain damage by increasing reliability of the detected features and automatically assessing a morphology of the ABP pulse via dicrotic notch classification.

DESCRIPTION OF DRAWINGS

FIG. 1 schematically illustrates a feature detecting device of an ABP waveform according to an exemplary embodiment of the present invention.

FIG. 2 illustrates a feature of an ABP waveform which is considered in an exemplary embodiment of the present invention.

FIG. 3 is a flowchart illustrating a feature detecting method of an ABP waveform according to an exemplary embodiment of the present invention.

FIG. 4 is a flowchart for explaining a method of detecting a systolic peak according to an exemplary embodiment of the present invention in detail.

FIG. 5 is an exemplary embodiment in which a method of detecting a morphological feature of an ABP waveform according to an exemplary embodiment of the present invention is applied to an ABP waveform of an actual clinical patient.

| [Description of Main Reference Numerals of Drawings] | |
|---|---|
| 10: Pulse onset | 20: Systolic peak |
| 30: Dicrotic notch | 32: Normal notch |
| 34: Transient notch | 40: Dicrotic peak |
| 100: Sensor unit | 200: Memory |
| 300: Processing unit | |

BEST MODE

Hereinafter, the present invention will be described more fully hereinafter with reference to the accompanying drawings, in which exemplary embodiments of the invention are shown. However, the present invention can be realized in various different forms, and is not limited to the exemplary embodiments described herein. Accordingly, the drawings and description are to be regarded as illustrative in nature and not restrictive. Like reference numerals designate like elements throughout the specification.

Throughout this specification and the claims that follow, when it is described that an element is "coupled" to another element, the element may be "directly coupled" to the other element or "electrically coupled" to the other element through a third element. In addition, unless explicitly described to the contrary, the word "comprise" and variations such as "comprises" or "comprising", will be understood to imply the inclusion of stated elements but not the exclusion of any other elements.

Hereinafter, a device and a method of detecting a feature of an ABP waveform according to an exemplary embodiment of the present invention will be described in detail with reference to the drawings.

FIG. 1 schematically illustrates a feature detecting device of an ABP waveform according to an exemplary embodiment of the present invention.

Referring to FIG. 1, a feature detecting device of an ABP waveform according to an exemplary embodiment of the present invention includes a sensor unit 100, a memory 200, a processing unit 300, and a display 400. In this case, the sensor unit 100 and the display unit 400 may be included in the feature detecting device of an ABP waveform according to an exemplary embodiment of the present invention or separately provided outside the feature detecting device of an ABP waveform.

The sensor unit 100 includes an analog amplifier (not illustrated) and a digital converter (not illustrated) and measures an ABP to convert the ABP into a digital signal.

In the memory 200, a feature detecting application of an ABP waveform may be stored and the ABP waveform data which is converted into a digital signal may be stored. In this case, the memory 200 includes an arbitrary method or technique for storing information such as a computer readable command, a data structure, a program module, and other data or a volatile and non-volatile, a removable and non-removable medium which is implemented by an arbitrary method or a technique. For example, the memory 200 includes a NAND flash memory such as a read only memory (ROM), a random access memory (RAM), a magnetic tape, a magnetic disk, a flash memory, an optical data storage device, a compact flash (CF) card, a secure digital card, a memory stick, a solid state driver (SSD), and a micro SD card and a magnetic computer storage device such as a hard disk driver (HDD).

The processing unit 300 deducts derivatives from ABP waveform data stored in the memory 200 in accordance with execution of a feature detecting application to detect a morphological feature of the ABP waveform.

The display 400 displays the ABP waveform detected by the sensor unit 100 and features of the detected ABP waveform in real time and also displays respective features with different colors.

FIG. 2 illustrates a feature of an ABP waveform which is considered in an exemplary embodiment of the present invention.

Referring to FIG. 2, the feature of the ABP waveform considered in the exemplary embodiment of the present invention includes a pulse onset 10, a systolic peak 20, a dicrotic notch 30, and a dicrotic peak 40. The feature of the ABP waveform is closely related to blood circulation.

Specifically, the pulse onset 10 is related to an opening time of an aorta valve. Further, the systolic peak 20 reflects that blood is discharged when an intraventricular pressure exceeds an arterial pressure to open a semilunar valve and arterial wave reflection. The dicrotic notch 30 is related to the closing of the aorta valve. Therefore, the related art is utilized to detect a feature by analyzing an ABP and diagnose a heart condition using the feature. However, the ABP waveform is exposed to various noises and a shape of the waveform is easily modified according to a respiratory or ABP measuring method and a measured site so that it is difficult to detect a feature. Further, there is a limit to an ability of clinical specialists to directly analyze a vast amount of data generated during a process of consistent monitoring by arterial cannula insertion.

Therefore, the feature detecting device of an ABP waveform according to an exemplary embodiment of the present invention automatically extracts a feature of the ABP waveform in accordance with execution of a feature detecting application to enable consistent monitoring. Further, the feature is automatically detected so that a reliability of a detected feature is increased and the dicrotic notch 30 is classified into a normal notch and a transient notch to provide many advantages in clinical situations, especially in diagnosis and prognosis of a patient with a brain damage.

Hereinafter, a feature detecting method of a feature detecting device of an ABP waveform according to an exemplary embodiment of the present invention will be described in detail with reference to FIG. 3.

FIG. 3 is a flowchart illustrating a feature detecting method of an ABP waveform according to an exemplary embodiment of the present invention.

Referring to FIG. 3, the feature detecting method of an ABP waveform includes a step s100 of searching a peak and a trough, a step s200 of detecting a systolic peak, a step s300 of detecting a pulse onset, a step s400 of extracting a candidate of a dicrotic notch, a step s500 of detecting a dicrotic notch and a dicrotic peak, and a step s600 of classifying the detected dicrotic notch into a normal notch and transient notch.

First, in the step s100 of searching a peak and a trough, the processing unit 300 deducts a linear derivative of an ABP waveform and sets a point at which a value of the derivative is zero, that is, inflection points of the ABP waveform as a peak or a trough.

Specifically, when a measurement time of an i-th signal of the ABP waveform is $t_i$, a measured pressure value is $P_i$, a linear derivative at the time $t_i$ is $P'_i$, if $p_{i-1} < p_i$ at an inflection point satisfying that $p'_{i-1} > 0$ and $p'_i < 0$, the processing unit 300 sets points corresponding to $t_i$ as peak points. Further, if $p_{i-1} > p_i$, the processing unit 300 sets points corresponding to $t_{i-1}$ as peak points.

In the meantime, if $p_{i-1} > p_i$ at an inflection point satisfying that $p'_{i-1} < 0$ and $p'_i > 0$, the processing unit 300 sets points corresponding to $t_i$ as trough points. Further, if $p_{i-1} < p_i$, the processing unit 300 sets points corresponding to $t_{i-1}$ as trough points.

The peak points and trough points searched in the above step may be candidates of characteristic points such as a systolic peak 20 which has an actual clinical significance.

Next, in the step s200 of detecting a systolic peak 20, the systolic peak 20 is detected from peak points searched in the previous step s100. In this case, the method of detecting a systolic peak 20 according to an exemplary embodiment of the present invention is based on an assumption that the systolic peak 20 is a peak appearing after a maximum inflection.

FIG. 4 is a flowchart for explaining a method of detecting a systolic peak according to an exemplary embodiment of the present invention in detail.

Referring to FIG. 4, the step s200 of detecting a systolic peak according to an exemplary embodiment of the present invention includes a step s210 of calculating a maximum value and an average during an arbitrary time, a step s220 of extracting candidates of a systolic peak, a step s230 of calculating an average time interval and an average pressure value of candidates of a systolic peak, and a step s240 of detecting a systolic peak.

First, at a beginning of an ABP waveform analysis, a maximum value and an average of the ABP waveform are calculated during an arbitrary time (s210).

Next, in the step s220 of extracting candidates of a systolic peak, peaks which exceed the calculated average and are close to the maximum value are collected in a time window. In this case, a length of the time window depends on an arbitrary time when the maximum value and the average executed in step s210 are analyzed. For example, when the candidates of the systolic peak are collected after analyzing the maximum value and the average in a waveform existing within previous three seconds in step s210, as the collected candidates of the systolic peak are increased, the length of the time window has a range from a minimum of 3 seconds to a maximum of 30 seconds.

Next, an average time interval $meanV_j$ of peaks collected in the time window and an average pressure value $meanP_j$ are calculated (s230). Here, the time interval $V_j$ refers to a time interval between a j-th peak collected in the time window and a previous peak.

Next, in the step s240 of detecting systolic peaks, the systolic peaks are detected based on the average time interval $meanV_j$ and the average pressure value $meanP_j$ calculated in the time window. Specifically, as the systolic peak 20, j-th peaks which satisfy $|meanP_j - P_j| < meanP_j*0.15$ and $|meanV_j - V_j| < meanV_j*0.15$ among the candidates of the systolic peak extracted in the time window are selected.

Referring to FIG. 3 again, in the step s300 of detecting a pulse onset 10, trough points appearing before the maximum inflection of the derivative, that is, existing immediately before the systolic peak 20 are detected as the pulse onset.

Next, in the step s400 of extracting a candidate of dicrotic notch, a candidate of the dicrotic notch 30 is extracted based on a magnitude and a measurement time of the systolic peak 20.

Generally, the dicrotic notch 30 may be classified into four types. Specifically, in a first type, a notch appears as a distinct notch appearing after the negative inflection on the derivative and in a second type, a flat portion appears in the ABP waveform after the systolic peak 20. In a third type, a decreasing degree of a pressure value of the ABP waveform in the systolic peak 20 is reduced, that is, a change of a gradient is reduced. In the last type, the notch is not generated. Therefore, according to the method of extracting a candidate of the dicrotic notch according to an exemplary embodiment of the present invention, the candidates are extracted in consideration of all four types of dicrotic notches 30 which are described above. In this case, since the second and third types of dicrotic notch 30 are similar to each other, high user dependency is accompanied to distinguish the second type and the third type. Therefore, in the present invention, two types are treated together for automated analysis.

Therefore, according to a specific method of extracting a candidate of a dicrotic notch 30 according to the exemplary embodiment of the present invention, a time interval of the systolic peak 20 is newly defined first, and a search window is set to extract the candidate of the dicrotic notch 30.

When a measurement time of a k-th systolic peak 20 is $\tau_k$ and an amplitude (magnitude) of the systolic peak 20 at $\tau_k$ is $\alpha_k$, and the time interval $V_k$ between the systolic peaks 20 represents a time interval between the k-th peak and a k−1-th peak which is a previous peak. Next, one point of the ABP waveform within a time interval from $\tau_k$ to $\tau_{k+1}$ defined as $V_k$ is defined as $x_{k,i}$.

According to an exemplary embodiment of the present invention, a time when a flat portion appears in the ABP waveform after the systolic peak 20 and a time when a decreasing angle of the ABP is reduced flexibly vary depending on a heartbeat. Therefore, a range from $\tau_k + V_k*0.1$ to $\tau_k + V_k*0.25$ in which a length of at least 200 ms after the systolic peak 20 is guaranteed is set as a search window.

Next, a point $x_{k,i}$ at which a derivative value which is included in the search window range, that is, $y'_{k,i}$ satisfies Equation 1 is selected as a candidate of the dicrotic notch 30. In this case, Equation 1 is represented below.

$$-0.05 \times \frac{\alpha_k}{V_k} < y'_{k,i} < 0 \qquad \text{[Equation 1]}$$

Next, according to the feature detecting method of an ABP waveform according to an exemplary embodiment of the present invention, after the step of extracting a candidate of a dicrotic notch 30, a point having a lowest pressure value among the candidates is set as the dicrotic notch 30 and a peak which is searched immediately after the dicrotic notch is detected as a dicrotic peak 40 (s500).

Next, the detected dicrotic notches are classified into a normal notch and a transient notch (s600). As a method of classifying the normal notch and the transient notch, a fact that a height of a dicrotic peak is low or not observed at all in the transient notch is used. Therefore, a magnitude of the dicrotic peak 40 and a magnitude of a systolic peak 20 are compared to distinguish whether the searched dicrotic notch 30 is a normal notch or a transient notch. In this case, as a method of determining a normal notch 32, Equation 2 may be used.

$$\beta_k > \alpha_k * 0.05 \quad \text{[Equation 2]}$$

Here, $\alpha_k$ is an amplitude of a systolic peak and $\beta_k$ is an amplitude of a dicrotic peak. Therefore, when Equation 2 is satisfied, the searched dicrotic notch 30 is classified as the normal notch 32 and when Equation 2 is not satisfied, the searched dicrotic notch 30 is classified as the transient notch 34.

In the meantime, the feature detecting method of an ABP waveform according to an exemplary embodiment may further include a step of analyzing a frequency of a transient notch to automatically predict a prognosis of a patient with a brain damage after the step s600. Alternatively, the feature detecting method of an ABP waveform according to an exemplary embodiment may further include a step of calculating various parameters such as a latency from a pulse onset to a dicrotic notch and a latency from the pulse onset to a systolic peak to automatically predict a prognosis of a patient with a brain damage.

For example, when a ratio of the transient notch is higher than that of the normal notch in the detected dicrotic notch or when the normal notch disappears and the transient notch is increased during the monitoring of the patient with a brain damage, it is diagnosed that an autoregulation function of the patient with a brain damage is abnormal or it is judged that the prognosis of the patient with a brain damage is not good.

FIG. 5 is an exemplary embodiment in which a morphological feature detecting method of an ABP waveform according to an exemplary embodiment of the present invention is applied to an ABP waveform of an actual clinical patient.

FIG. 5A is data obtained by measuring ABP waveforms of patients A and B and FIG. 5B is a graph of classifying a pulse onset 10, a systolic peak 20, and a normal notch 32 or a transient notch 34 according to the exemplary embodiment of the present invention to detect the dicrotic notch 30.

Detecting precisions of a feature of an ABP waveform according to an exemplary embodiment of the present invention are measured for the pulse onset 10, the systolic peak 20, the dicrotic notch 30, and the dicrotic peak 40. As an exemplary embodiment, for thirty patients, ten ABP waveform data is randomly extracted for every patient. With respect to a total of 300 waveforms, features are manually detected by a skilled observer and features are automatically detected according to an exemplary embodiment of the present invention. In this case, a feature detection result according to the exemplary embodiment of the present invention is not exposed to the observer. A difference of absolute values of a measurement time at each manually selected point and a measurement time at an automatically detected point of one ABP waveform is calculated as an error and an error which is 30 ms or less is ignored. By this method, precisions of 99.3%, 98.3%, 92.3%, and 92.6% are calculated for the pulse onset, the systolic peak, the dicrotic notch, and the dicrotic peak, respectively.

As described above, when a morphological feature detecting method of an ABP according to an exemplary embodiment of the present invention is used, the feature is detected with a high precision and various parameters required to describe a condition in the brain of the patient may be deducted using the detected major points. According to a related study of the related art, a phenomenon that the dicrotic notch changes from the normal notch to a status such as a transient notch and eventually disappears is known to indicate a condition such as vessel expansion and contraction. Therefore, a condition of a cardiovascular system and a cerebrovascular system is understood through observation of a change of the dicrotic notch to which the change of a diameter of the blood vessel is reflected. Specifically, when the condition of the cerebrovascular system is described, it is used for inspection of a cerebral autoregulation ability of the patient. The cerebral autoregulation ability is an automatic regulation mechanism which adjusts a diameter of a blood vessel to maintain an appropriate blood flow. When the mechanism does not normally operate, a risk of an ischemic brain damage or a stroke is increased.

As an example, as a result of applying the morphological feature detecting method according to the present invention to an ABP waveform obtained from a patient with a traumatic brain damage, a ratio of the dicrotic notch in the entire waveform, specifically, a ratio of a waveform having a normal notch is significantly lower in patients who died than in survivors. This suggests that the waveform from which the dicrotic notch disappears is used as a simple indicator indicating that a cerebral autoregulation of the patient is abnormal.

In addition, according to the present invention, various approaches are available for diagnosis and prognosis of the patient by deducting various parameters such as a latency from the pulse onset to the dicrotic notch, a latency from the systolic peak to the dicrotic notch, and a magnitude of an amplitude of each peak. Further, since the ABP waveform has a similar waveform to the transcranial Doppler (TCD) which is measured through an ultrasonic wave, the present invention may extend to be similarly applied to a signal obtained from the TCD.

An exemplary embodiment of the present invention may be implemented as a recording medium including a command which is executed by a computer such as a program module which is executed by the computer. The computer readable medium may be an arbitrary available medium which is accessed by a computer and includes all of a volatile and non-volatile medium, a removable and non-removable medium.

Further, the computer readable medium may include all of a computer storage medium and a communication medium. The computer storage medium includes an arbitrary method or a technique for storing information such as a computer readable command, a data structure, a program module, and other data or a volatile and non-volatile, a removable and non-removable medium which is implemented by an arbitrary method or a technique. A communication medium includes a typical computer readable command, a data structure, a program module, or other data of a modified data signal such as a carrier wave or other transmitting mechanism and also includes an arbitrary information transfer medium.

The morphological feature detecting device of an ABP waveform according to the present invention may be implemented as a computer readable code in computer readable recording media. The computer readable recording media include all kinds of recording media in which data, which are capable of being read by a computer system, are stored. For example, the recording media may include a read only memory (ROM), a random access memory (RAM), a magnetic tape, a magnetic disk, a flash memory, and an optical data storage device. Further, the computer readable recording media are distributed on computer systems connected through the computer communication network, and thus the computer-readable recording media may be stored and executed as the readable code by a distribution scheme.

The above-description of the present invention is illustrative only and it is understood by those skilled in the art that the present invention may be easily modified to another specific type without changing the technical spirit of an essential feature of the present invention. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present invention is represented by the claims to be described below rather than the detailed description, and it is to be interpreted that the meaning and scope of the claims and all the changes or modified forms derived from the equivalents thereof come within the scope of the present invention.

The invention claimed is:

1. A feature detecting method of an arterial blood pressure (ABP) waveform, the method comprising:
   identifying a plurality of peaks and a plurality of troughs within the arterial blood pressure waveform;
   detecting a systolic peak based on a time interval between an identified peak and an identified neighboring peak and an average pressure value;
   detecting a pulse onset with respect to an identified trough directly before the systolic peak;
   extracting candidates of a dicrotic notch based on a magnitude of the systolic peak and a measurement time;
   detecting a point having a lowest pressure value among the candidates of the dicrotic notch as a detected dicrotic notch and detecting a dicrotic peak based on the detected dicrotic notch; and
   classifying the detected dicrotic notch into a normal notch and a transient notch;
   wherein detecting of the systolic peak is based on the average time interval and the average pressure value;
   wherein a peak which simultaneously satisfies Equations 1 and 2 is detected as the systolic peak,
   Equation 1 is $|meanP_j - P_j| < meanP_j * 0.15$ Equation 2 is $|meanV_j - V_j| < meanV_j * 0.15$; and wherein $V_j$ indicates a time interval between a j-th peak and an previous (j-1-th) peak, $meanV_j$ indicates an average time interval, and $meanP_j$ indicates an average pressure value.

2. The method of claim 1, wherein in the classifying of the detected dicrotic notch into a normal notch and a transient notch, when a pressure value between the dicrotic notch and the dicrotic peak is higher than a magnitude of the systolic peak by a predetermined ratio, the dicrotic notch is classified as the normal notch, and when a pressure value between the dicrotic notch and the dicrotic peak is lower than a magnitude of the systolic peak by a predetermined ratio, the dicrotic notch is classified as the transient notch.

3. The method of claim 1, further comprising:
   analyzing a frequency of the transient notch to automatically predict a prognosis of a patient with a brain damage.

4. The method of claim 1, further comprising:
   calculating a latency from the pulse onset to the detected dicrotic notch or a latency from the systolic peak to the detected dicrotic notch to automatically predict a prognosis of a patient with a brain damage.

5. A feature detecting device of an ABP waveform, the device comprising:
   a memory in which a feature detecting application of an ABP waveform is stored; and
   a processing unit which is aligned to interface with the feature detecting application;
   wherein the processing unit is configured to
     receive an ABP waveform from a sensor unit,
     convert the received ABP waveform signal into digital data to store the converted digital data in the memory,
     according to the execution of the feature detecting application, identify a plurality of peaks and a plurality of troughs within the ABP waveform,
     detect a systolic peak based on an time interval between an identified peak and an identified neighboring peak and an average pressure value,
     detect a pulse onset with respect to an identified trough directly before the systolic peak,
     extract candidates of a dicrotic notch based on a magnitude of the systolic peak and a measurement time to detect a point having a lowest pressure value among the candidates of the dicrotic notch as a detected dicrotic notch,
     detect a dicrotic peak based on the detected dicrotic notch,
     classify the detected dicrotic notch into a normal notch and a transient notch;
   wherein the processing unit is further configured to detect a peak which simultaneously satisfies Equations 3 and 4 as the systolic peak,
   Equation 2 is $meanP_j - P_j| < meanP_j * 0.15$ Equation 4 is $meanV_j - V_j| < meanV_j * 0.15$; and wherein $V_j$ indicates a time interval between a j-th peak and a previous peak, $meanV_j$ indicates an average time interval, and $meanP_j$ indicates an average pressure value.

6. The device of claim 5, further comprising:
   a sensor unit which detects the detected ABP waveform; and
   a display which displays the detected ABP waveform, the detected pulse onset, systolic peak, dicrotic notch, and dicrotic peak in a real time.

7. The device of claim 6, wherein the display displays the normal notch and the transient notch with different colors.

8. The device of claim 5, wherein when a pressure value between the dicrotic notch and the dicrotic peak is higher than a magnitude of the systolic peak by a predetermined ratio, the processing unit classifies the dicrotic notch as a normal notch, and when a pressure value between the dicrotic notch and the dicrotic peak is lower than a magnitude of the systolic peak by a predetermined ratio, the processing unit classifies the dicrotic notch as a transient notch.

9. A non-transitory computer readable medium having recorded thereon an executable program for executing a feature detecting method of an atrial blood pressure (ABP) waveform of claim 1.

* * * * *